(12) United States Patent
Evans et al.

(10) Patent No.: US 9,931,449 B2
(45) Date of Patent: Apr. 3, 2018

(54) ELECTRICAL BREAST PUMP AND SYSTEM

(71) Applicants: Jeremy Patrick Evans, Vernon Hills, IL (US); Terry Chung, Kildeer, IL (US); Jordan Linn, Palatine, IL (US); David Shao Ling, Vernon Hills, IL (US); Joshua Stoia, Wheeling, IL (US)

(72) Inventors: Jeremy Patrick Evans, Vernon Hills, IL (US); Terry Chung, Kildeer, IL (US); Jordan Linn, Palatine, IL (US); David Shao Ling, Vernon Hills, IL (US); Joshua Stoia, Wheeling, IL (US)

(73) Assignee: Ameda, Inc., Buffalo Grove, IL (US)

( * ) Notice: Subject to any disclaimer, the term of this patent is extended or adjusted under 35 U.S.C. 154(b) by 399 days.

(21) Appl. No.: 14/725,739

(22) Filed: May 29, 2015

(65) Prior Publication Data
US 2016/0346446 A1 Dec. 1, 2016

(51) Int. Cl.
*A61M 1/06* (2006.01)
*A61M 1/00* (2006.01)

(52) U.S. Cl.
CPC ............ *A61M 1/06* (2013.01); *A61M 1/0031* (2013.01); *A61M 1/0068* (2014.02)

(58) Field of Classification Search
CPC ................. A61M 1/06; A61M 1/0037; A61M 2205/3337; A61M 1/0033
USPC ......................................................... 604/74
See application file for complete search history.

(56) References Cited

U.S. PATENT DOCUMENTS

| | | | |
|---|---|---|---|
| 2,747,714 A | 5/1956 | Eason | |
| 3,694,020 A | 9/1972 | Becker et al. | |
| 4,286,668 A | 9/1981 | McCormick | |
| 4,422,835 A | 12/1983 | McKee | |
| 4,484,732 A | 11/1984 | Gould | |
| 4,607,596 A * | 8/1986 | Whittlestone | A01J 5/04 119/14.02 |
| 4,749,342 A | 6/1988 | Fritsch | |
| 4,773,305 A * | 9/1988 | Nissels | F04B 53/143 277/448 |
| 4,827,976 A | 5/1989 | Heimbrodt et al. | |
| 4,924,629 A | 5/1990 | Smith et al. | |
| 5,125,429 A | 6/1992 | Ackroyd et al. | |
| 5,257,572 A | 11/1993 | Jakobi et al. | |
| 5,348,036 A | 9/1994 | Oksanen et al. | |
| 5,954,690 A * | 9/1999 | Larsson | A61M 1/0068 604/152 |

(Continued)

FOREIGN PATENT DOCUMENTS

DE 3740159 A1 12/1988

OTHER PUBLICATIONS http://www.hycontrol.com/docs/13-pn-file.pdf; Controlair, Inc.; Rolling Diaphragm Air Cylinders (The friction free alternative).

(Continued)

*Primary Examiner* — Nathan R Price
*Assistant Examiner* — John Doubrava
(74) *Attorney, Agent, or Firm* — Vedder Price P.C.

(57) ABSTRACT

An electrical breast pump may include a permanently unobstructed continuous passageway across the diaphragm and a rolling diaphragm that is movable between a vent orientation and a vacuum orientation, or a vent piston configured to actuate a closure between a vent orientation and a vacuum orientation so that a pressure chamber is selectively in direct communication with atmospheric pressure.

11 Claims, 16 Drawing Sheets

(56) References Cited

U.S. PATENT DOCUMENTS

| | | | |
|---|---|---|---|
| 6,000,416 | A | 12/1999 | Kingsford et al. |
| 6,006,651 | A | 12/1999 | Pierce et al. |
| 6,383,163 | B1 | 5/2002 | Kelly et al. |
| 6,899,530 | B2 | 5/2005 | Lehrke et al. |
| 7,475,863 | B2 | 1/2009 | Donovan |
| 8,052,635 | B1 | 7/2011 | Kelly et al. |
| 8,137,305 | B2 | 3/2012 | Kelly et al. |
| 2014/0094748 | A1* | 4/2014 | Hong .................. A61M 1/06 604/74 |

OTHER PUBLICATIONS http://www.swagelok.com/downloads/webcatalogs/EN/MS-02-230.pdf; Swagelok; Pressure Regulators K Series.
http:/www.singervalve.com/hs-fs/hub/230327/file-2358783879-pdf/Whitepapers/Technical_and_Sizing.pdf; Singer Valve; Automatic Control Valves (Technical & Sizing Information).

\* cited by examiner

ELECTRICAL BREAST PUMP AND SYSTEM

FIELD OF THE DISCLOSURE

The present disclosure generally relates to electrical breast pumps and electrical breast pump systems. More particularly, the present disclosure relates to a simple electrical breast pump and electrical breast pump system for extracting milk from a human breast that quickly attains a desired setting.

BACKGROUND

Most prior art breast pumps designed for extracting milk are concerned only with controlling the rate at which a negative pressure is applied to the breast and, in some cases, the amount of negative or vacuum pressure. However, the amount of milk volume obtained in response to a constant average suction is quite low compared to that obtained by a suckling infant.

Recently, breast pump systems have been introduced that use a constantly running positive displacement vacuum pump, sense and monitor the negative pressure or vacuum and open a valve in response to the sensed vacuum in excess of the vacuum limit in order to decrease the vacuum to a desired point. Such systems are complex, which reduces reliability, and costly, which discourages breast feeding.

Other conventional breast pump systems, see FIGS. 3 and 4, include a pump assembly 10 having a reciprocating piston assembly 20 driven by a reversible motor 14. A rolling diaphragm 22 is connected via circumferential tension at an inner end 24 to a center post 26 of the piston assembly 20 and at an outer end 28 captured between the piston housing 30 and the drive housing 32. The vent piston 34 includes, in FIG. 3, a vent 36 formed as a bore that extends from a distal end 38 (at the top wall 37) to a proximal end 40 disposed adjacent the lower end of a side wall 42 of the vent piston 34, and in FIG. 4, a vent 36 formed as a bore that extends through a side wall 42 of the vent piston 34 to a channel 44 formed around the center post 26. Both the vents 36 enable the pressure chamber 46 to communicate with a portion 48 of the diaphragm 22 adjacent to connection to the center post 26.

In theory, it was thought and desired that the portion 48 would overcome the circumferential tension when a slight positive pressure was generated in the pressure chamber 46 when the vent piston 34 was disposed adjacent a port formed in an end wall of the piston housing 30 (e.g., near maximum extension) and move or deflect in the direction of the threaded piston 50 to facilitate defining an intermittent passage to atmosphere every time the vent piston 34 reached near maximum extension from the drive screw 52. However, it was discovered through testing and operation that the portion 48 was not consistently moving or deflecting as desired and that the portion 48 was not moving at maximum extension of the piston assembly 20 in response to the slight positive pressure present in the pressure chamber 46 and/or the portion 48 was moving near the beginning of a vacuum retraction pull by the piston assembly 20 (in an opposite direction from what was desired) so that the desired vacuum is not achieved. In other words, the breast pump system was too closed or only somewhat intermittently openable to atmosphere resulting in painful constant increasing vacuum profiles or under vacuum profiles that take a considerable time to operate properly, raising distrust as to proper operation. As a result, the conventional breast pump system took on average at least 20-30 seconds to reach a consistent steady state pressure or vacuum recovery profile. Sometimes it would take longer and still further sometimes it would never reach the desired consistent steady state vacuum recovery profile.

FIG. 5 is a graph of pressure versus time, illustrating the conventional prior art breast pump system (as conceptually shown in FIG. 1 and including as pump assembly as shown in either FIG. 3 or FIG. 4) vacuum recovery profile. One will note that in concept nearly any breast pump system includes, as shown in FIG. 1, a pump assembly housing 54 (with the pump assembly 10 disposed within, but not shown in this FIG. 1), a pair of collection units 56 each connected via tubing to a single port of the pump assembly and including breast flanges 58. As shown in FIG. 5, neither of the flanges 58 experiences a quick vacuum recovery profile from a 0 mm Hg reading (i.e., atmospheric pressure), where the desired vacuum profile smoothly oscillates between 0 mm Hg and 200 mm Hg (for this testing purpose only, in practice the maximum vacuum is selectable by the user). Rather, one flange 58 experiences a weak but steadily increasing vacuum profile (i.e., the lower trace 60) and the other flange 58 experiences a weak, barely increasing vacuum profile (i.e., the upper trace 62). Usually, the lower trace 60 may stabilize at the desired or called for 200 mm Hg and the upper trace 62 will eventually match the vacuum recovery profile of the lower trace 60. However, a significant disadvantage is the discomfort of the nursing mother that discourages her from breast feeding with the unnecessary complications. Further, it has been commonly observed that the lower trace 60 and/or both traces 60, 62 may actually continue to increase the amount of vacuum until reaching a painful level (e.g., approximately 250-270 mm Hg) where the nursing mother must rest operation of the prior art device by deactivating the pump assembly and removing the flange. Thereafter, the entire process must start over, which most likely is a repeat of the vacuum recovery profile as shown in FIG. 5. Another situation where a quick vacuum recovery profile is desired is when there is an intermittent leak in the system. Obvious disadvantages are not only the discomfort and possible pain, but also the time delays and frustration and distrust with faulty operation.

Therefore, there is a need in the art for simple, reliable electrical breast pump and electrical breast pump system that quickly attains and maintains a desired setting regardless if starting anew, after a break or as a result of a system leak and that overcomes the disadvantages of the complex and unreliable prior art systems.

BRIEF DESCRIPTION OF THE DRAWINGS

The disclosure will be more readily understood in view of the following description when accompanied by the below figures and wherein like reference numerals represent the elements, wherein.

DETAILED DESCRIPTION OF THE PREFERRED EMBODIMENTS

Figure 1:
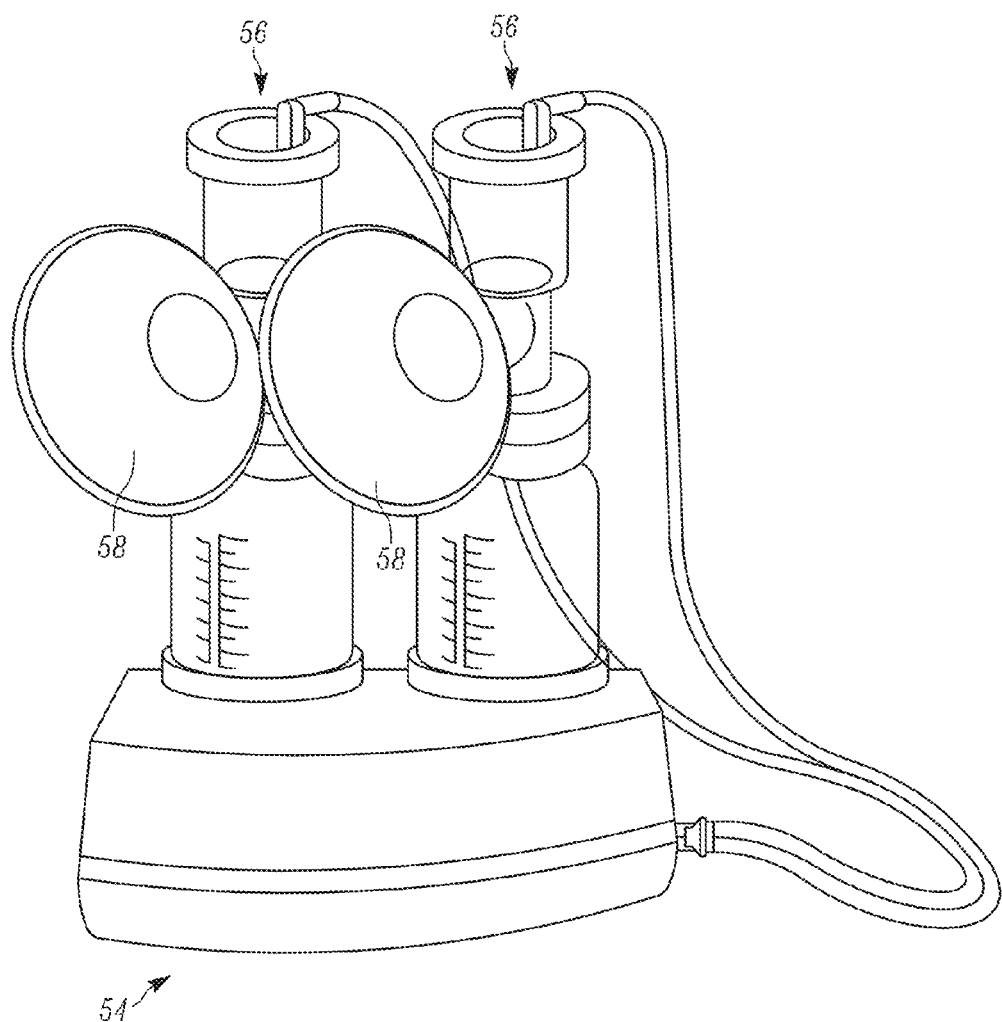
FIG. 1 illustrates a perspective view of one embodiment of an electrical breast pump system the present disclosure.

The following disclosure as a whole may be best understood by reference to the provided detailed description when read in conjunction with the accompanying drawings, drawing description, abstract, background, field of the disclosure, and associated headings. Identical reference numerals when found on different figures identify the same elements or a functionally equivalent element. The elements listed in the abstract are not referenced but nevertheless refer by association to the elements of the detailed description and associated disclosure.

Generally, an electrical breast pump as disclosed herein may include a permanently unobstructed continuous passageway that is disposed at atmospheric pressure and defined across a rolling diaphragm that is movable between a vent orientation and a vacuum orientation, or a vent piston configured to actuate a closure between a vent orientation and a vacuum orientation so that a pressure chamber is selectively in direct communication with atmospheric pressure.

In one aspect of the present disclosure, an electrical breast pump may include a housing assembly having a piston housing and a drive housing having an opening in direct communication with atmospheric pressure. A piston assembly may include a vent piston and a drive piston. The vent piston has a top wall, a channel defined by the top wall, a side wall and a center post, and a vent defined to extend through the side wall in communication with the channel. The drive piston having a top wall with a vent passage defined therethrough. A rolling diaphragm may include an outer end, an outer margin disposed adjacent the outer end. The outer end and outer margin are sealingly captured between the piston housing and the drive housing. An inner end and an inner margin disposed adjacent the inner end are sealingly captured between the vent piston and the drive piston to cooperatively define a pressure chamber between the diaphragm, piston housing and vent piston. A permanently unobstructed continuous passageway across the diaphragm that is disposed at atmospheric pressure is defined by the vent, the channel, the inner end that is spaced from the center post, the vent passage and the opening. The diaphragm is movable between a vacuum orientation and a vent orientation in response to cyclic movement of the piston assembly. The vacuum orientation is defined when an outer opening of the vent is sealed by the diaphragm, and the vent orientation is defined when the outer opening of the vent is uncovered by the diaphragm so that the pressure chamber is in direct communication with atmospheric pressure via the permanently unobstructed continuous passageway across the diaphragm.

In other aspects of the present disclosure, the portion is the entirety of the inner end or is defined by the inner end having a crenelated contour. In another aspect, a plurality of ribs may extend from the center post to engage the inner end, or the center post may have a recess formed over a section adjacent the inner end. In yet another aspect, the vent piston may include a projection extending from the side wall into contact with the drive piston such that the portion engages the projection, or such that the inner edge engages the projection. In still another aspect, the drive piston may include an extension that projects from the top wall into contact with the vent piston such that the portion engages the extension, or such that the inner edge engages the extension. In a further aspect, an insert is disposed between the drive piston and the vent piston such that the portion engages the insert, or such that the inner edge engages the insert.

In a still further aspect of the present disclosure, a breast pump assembly may include a housing assembly including a piston housing and a drive housing having an opening in direct communication with atmospheric pressure. A piston assembly may include a vent piston and a drive piston. The vent piston may have a top wall and a channel defined by the top wall, a side wall, a hollow center post, a vent defined to extend through the side wall in communication with the channel, and a second vent defined to extend through a wall of the center post into the hollow. The drive piston may have a hollow center post with a vent passage defined therethrough so that the hollow center posts of the vent piston and the drive piston are longitudinally aligned in registration and sealingly connected. A rolling diaphragm may include an outer end, and an outer margin disposed adjacent the outer end that are sealingly captured between the piston housing and the drive housing. The diaphragm may also include an inner end circumferentially engages the center post, and an inner margin disposed adjacent the inner end is sealingly captured between the vent piston and the drive piston to cooperatively define a pressure chamber between the diaphragm, piston housing and vent piston. A permanently unobstructed continuous passageway across the diaphragm that is disposed at atmospheric pressure may be defined by the vent, the channel, the second vent, the hollow of the center post of the vent piston, the hollow of the center post of the drive piston, the vent passage and the opening. The diaphragm is movable between a vacuum orientation and a vent orientation in response to cyclic movement of the piston assembly, such that the vacuum orientation is defined when an outer opening of the vent is sealed by the diaphragm, and the vent orientation is defined when the outer opening of the vent is uncovered by the diaphragm so that the pressure chamber is in direct communication with atmospheric pressure via the permanently unobstructed continuous passageway across the diaphragm.

In another still further aspect of the present disclosure, a breast pump assembly may include a housing assembly having a piston housing having a vent passage in direct communication with atmospheric pressure and a closure movably connected to the piston housing that is configured to selectively seal the vent passage, and a drive housing. A piston assembly may include a vent piston configured to actuate the closure between a vent orientation and a vacuum orientation, and a drive piston. A rolling diaphragm may include an outer end, and an outer margin disposed adjacent the outer end that are sealingly captured between the piston housing and the drive housing. The diaphragm may also include an inner end and an inner margin that is sealingly captured between the vent piston and the drive piston to cooperatively define a pressure chamber between the diaphragm, piston housing and vent piston. The vent orientation is defined when the vent piston actuates the closure to open the vent passage so that the pressure chamber is in direct communication with atmospheric pressure and the vacuum orientation is defined when the vent piston is disengaged from the closure.

In another aspect of the present disclosure, the diaphragm may be disposed in the vent orientation between approximately 0.1 seconds and 1.2 seconds of each cycle of the piston assembly, depending on the speed setting or the extent of the longitudinal displacement of the piston assembly. In yet another aspect, the diaphragm may be disposed in the vent orientation between approximately 15% to 60% of each cycle of the piston assembly, depending on the speed setting or the extent of the longitudinal displacement of the piston assembly. In a preferred embodiment, the diaphragm is disposed in the vent orientation between 0.2 seconds and 1.0 second, or between approximately 20% and 50% of each cycle of the piston assembly, depending on the speed setting or the extent of the longitudinal displacement of the piston assembly.

FIGS. 2 and 6-13 show various different embodiments of an electrical breast pump assembly 100 that may include a permanently unobstructed continuous passageway that is disposed at atmospheric pressure and defined across a rolling diaphragm 122 that is movable between a vent orientation (FIG. 6) and a vacuum orientation (FIG. 7), or a vent piston 134 configured to actuate a closure between a vent orientation and a vacuum orientation so that a pressure chamber 146 is selectively in direct communication with atmospheric pressure 102.

Figure 2:
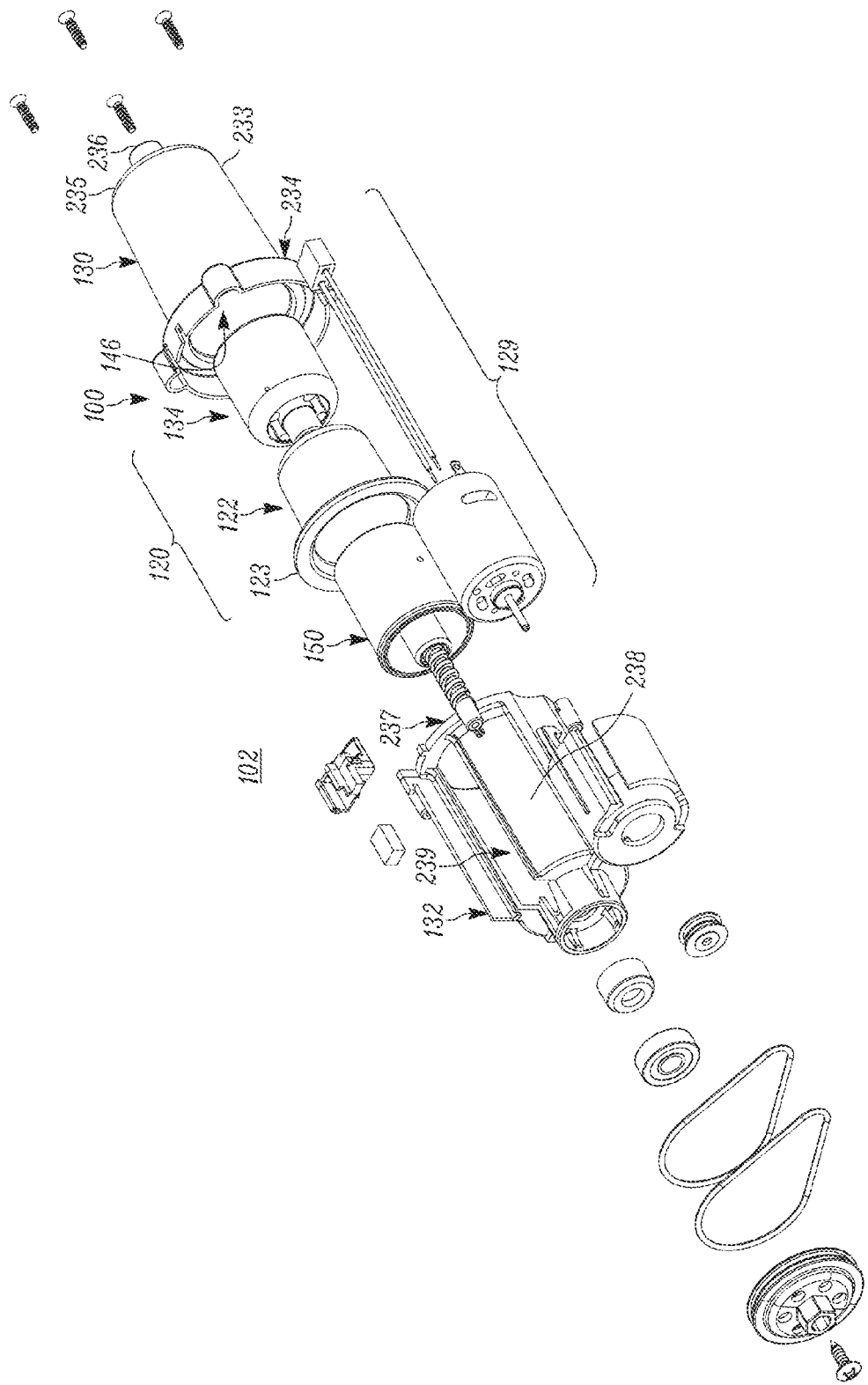
FIG. 2 illustrates an exploded view of one embodiment of a pump assembly of the present disclosure.
Figure 3:
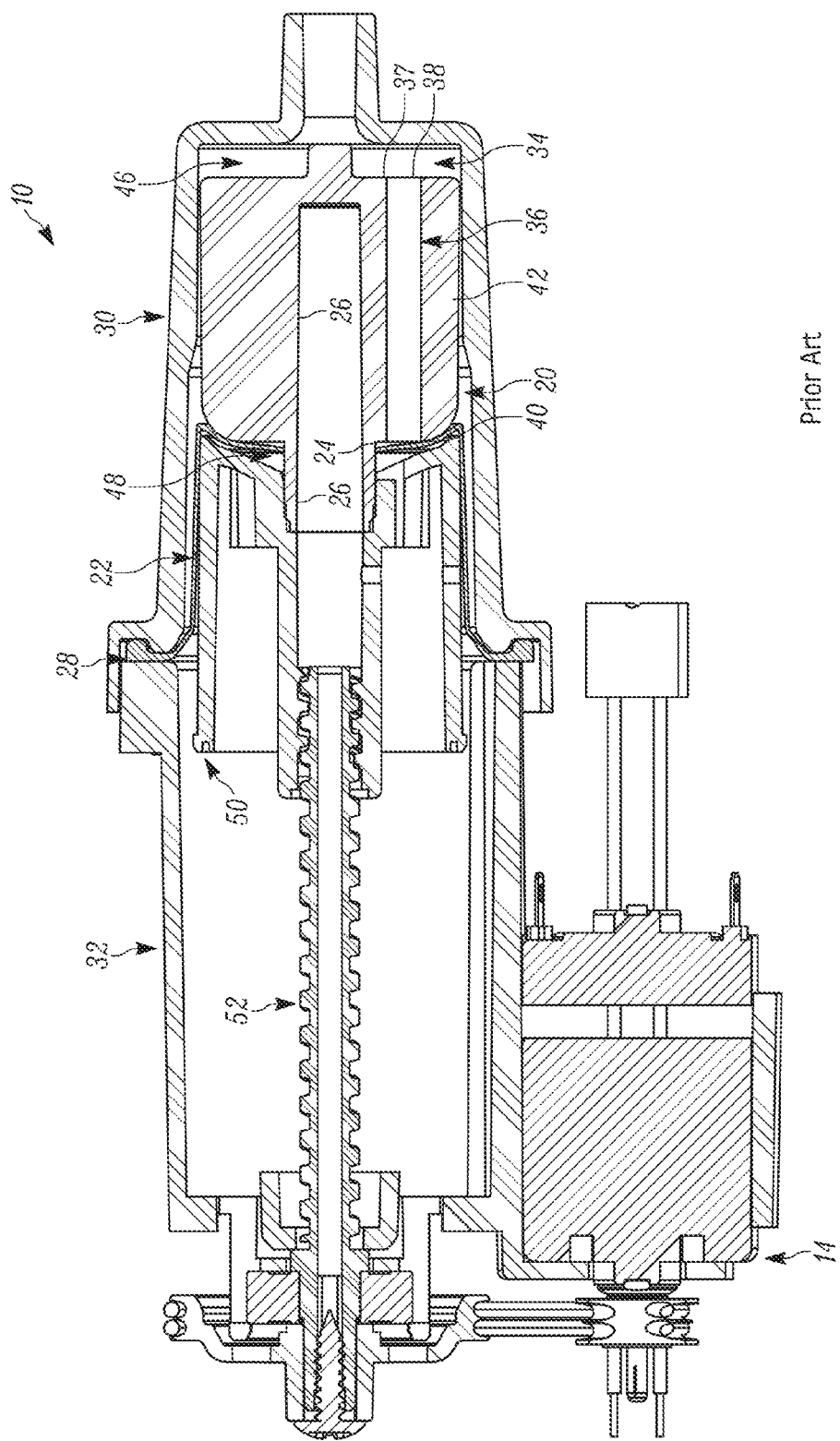
FIG. 3 illustrates a cross-section view of one embodiment of a pump assembly of a prior art electrical breast pump.
Figure 4:
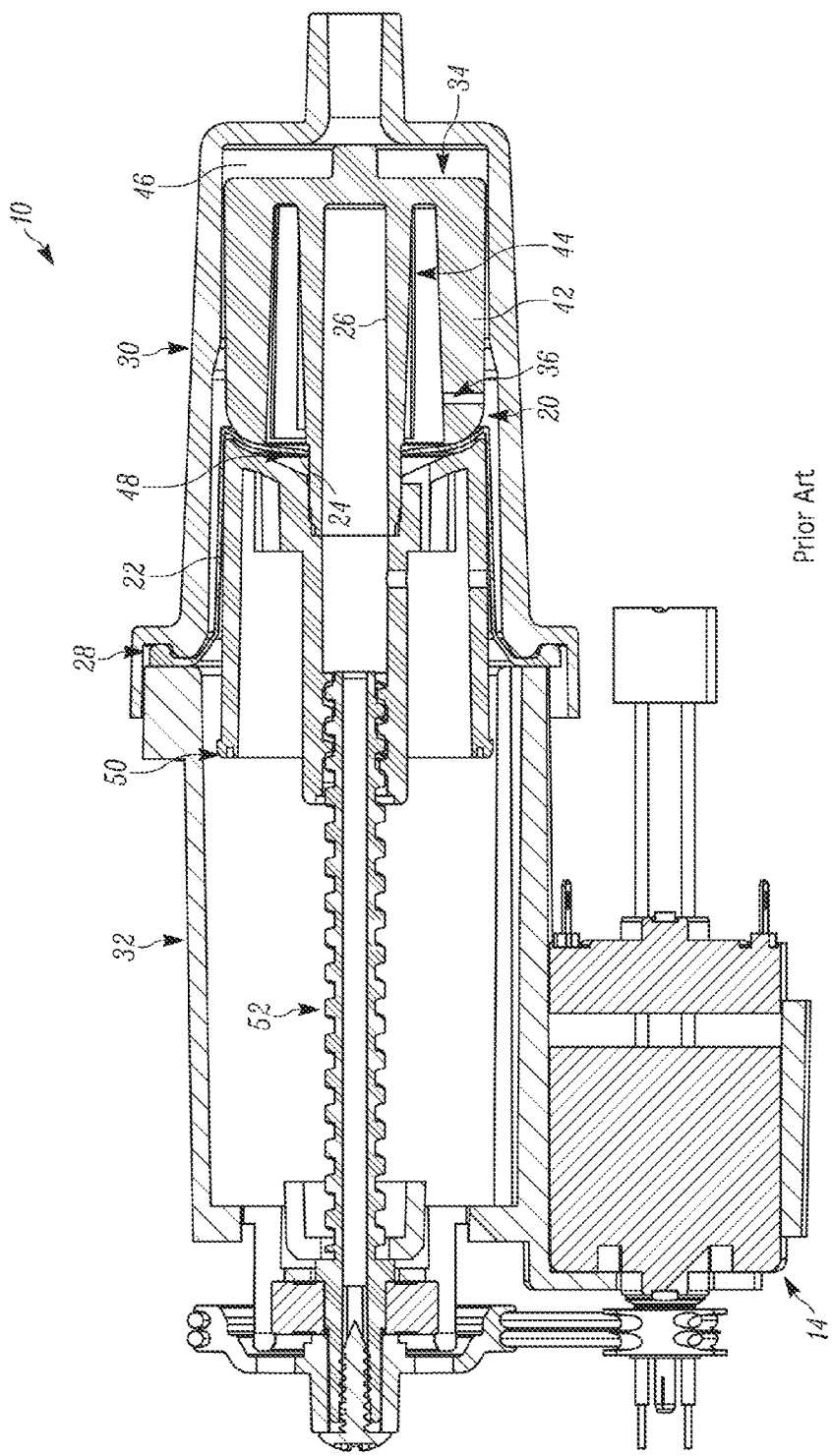
FIG. 4 illustrates a cross-section view of another embodiment of a pump assembly of a prior art electrical breast pump.
Figure 5:
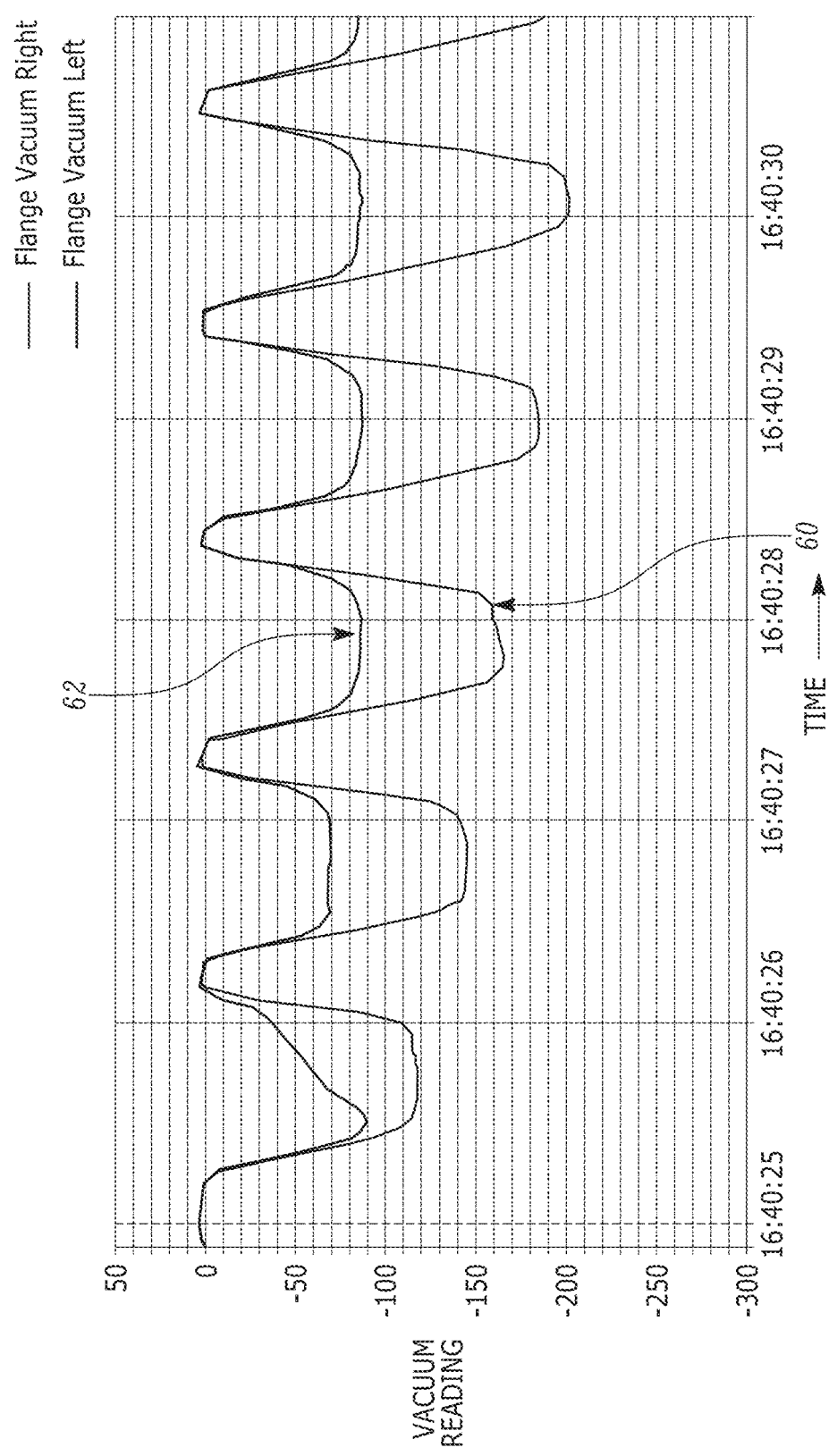
FIG. 5 is a graph of pressure versus time, illustrating a prior art breast pump system vacuum recovery profile.
Figure 6:
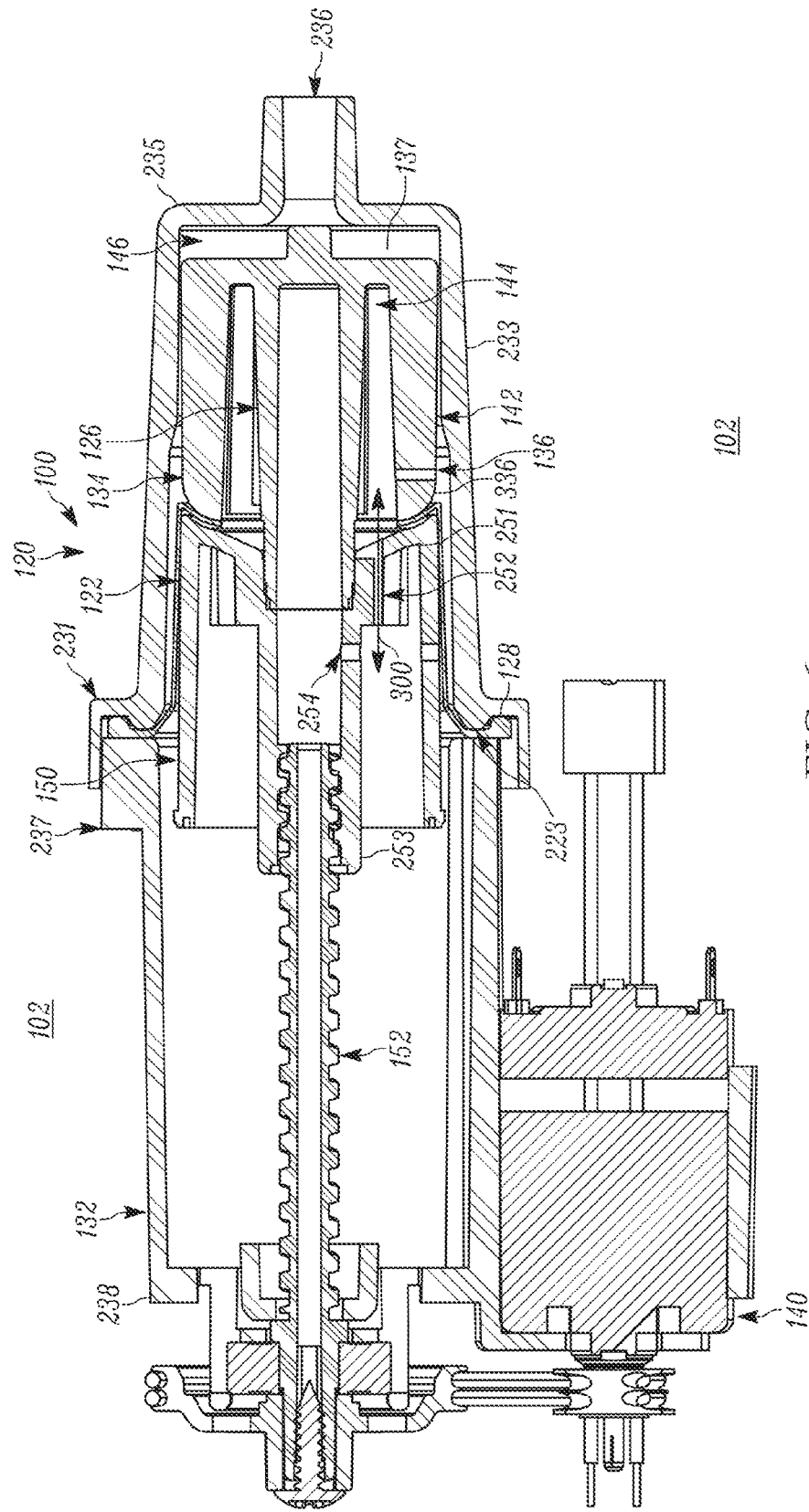
FIG. 6 illustrates a cross-section view of the pump assembly of FIG. 2 disposed in a vent orientation.
Figure 7:
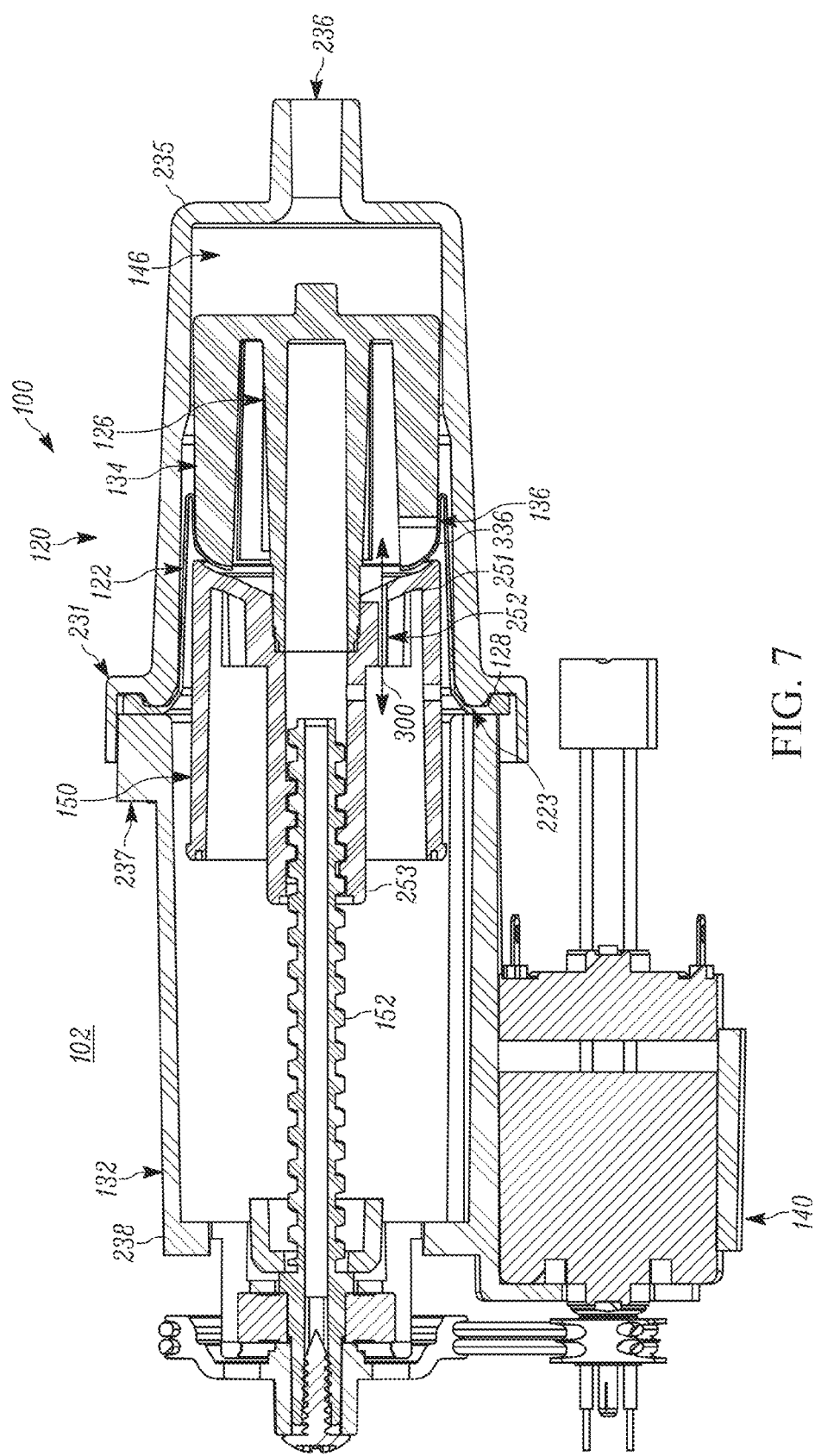
FIG. 7 illustrates a cross-section view of the pump assembly of FIG. 2 disposed in a vacuum orientation.

FIG. 2 illustrates an exploded view of one embodiment of a pump assembly 100 of the present disclosure. A housing assembly 129 may include a piston housing 130 and a drive housing 132. The piston housing 130 may include a flange 231 and a sidewall 233 have an exterior surface contour that is different from an interior surface contour. The exterior surface contour has a substantially linear taper from the flange to an end wall 235. The interior surface contour has a first component that is spaced from a piston assembly 120 sufficiently to allow a rolling diaphragm 122 to complete a one hundred eighty degree bend and accumulate in such space and a second component that is disposed in close proximity to a vent piston 134 to facilitate alignment and constrained movement thereof. Both of the first and second components have a slight taper or draft to facilitate removal from the mold, being preferable formed from plastic, synthetic, polymer, composite, etc. or the like types of materials. A single port 236 is preferable defined in the end wall 235. However, it is within the teachings of the present disclosure that multiple ports may be defined in the end wall 235. The drive housing 132 may include a flange 237 and a sidewall 238 having an opening 239 in direct communication with atmospheric pressure 102. The flanges 231 and 237 preferably cooperatively engage to sealingly capture an outer end 128 of the diaphragm 122 therebetween.

A piston assembly 120 in one embodiment may include at least a vent piston 134 and a drive piston 150 securely connected together such as by mechanical fastener, adhesive, welding, other connection techniques, etc. or the like.

The vent piston 134 may have a top wall 137 and a channel 144 defined by the top wall 137, a side wall 142 and a center post 126, such that the channel 144 is configured generally as an annular channel about the center post 126. Preferably, a vent 136 is defined as a bore or passageway that extends through the side wall 142 so that it is in direct communication with the channel 144. The drive piston 150 may have a top wall 251 with a vent passage 252 defined therethrough and a center post 253 having a proximal end (i.e., opposite the top wall 251) with an interior surface configured complementarily to engage a drive screw 152 such that rotation of the drive screw 152 by the reversible motor 140 selectively cyclically moves the piston assembly 120 in an oscillating movement from a start position where the vent piston 134 is disposed adjacent the end wall 235 to an adjustably selectable end position where the vent piston 134 is disposed at a desired extent from the end wall 235 in order to generate a pre-selected amount of vacuum pressure and then back to the start position to define a single cycle or piston stroke for which there is a corresponding vacuum profile curve. The piston assembly 120 is preferably formed from plastic, synthetic, polymer, composite, etc. or the like types of materials.

A rolling diaphragm 122 may include an outer end 128, an outer margin 223 disposed adjacent the outer end 128. It is within the teachings of the present disclosure that the outer margin 223 is configured as an area generally bounded by the outer end 128 and extending annularly toward an inner end 224 a sufficient distance in order to facilitate the desired functionality as described herein. One of skill in the art may recognize such configuration as generally rim- or ring-shaped. In one preferred embodiment, both of the outer end 128 and outer margin 223 are sealingly captured between the piston housing 130 and the drive housing 132. The diaphragm 122 may also include an inner end 224 and an inner margin 225 disposed adjacent the inner end 224. It is within the teachings of the present disclosure that the inner margin 225 is configured as an area generally bounded by the inner end 224 and extending annularly toward the outer end 128 a sufficient distance in order to facilitate the desired functionality as described herein. One of skill in the art may recognize such configuration as generally rim- or ring-shaped. In one embodiment, the inner margin 225 is sealingly captured between the vent piston 134 and the drive piston 150 to secure the diaphragm 122 in position and to cooperatively define a pressure chamber 146 as a volume between the diaphragm 122, piston housing 130 and vent piston 134. The diaphragm 122 is preferably formed from synthetic, polymer, rubber, latex, composite, etc. or the like types of materials.

A permanently unobstructed continuous passageway 300 across the diaphragm 122 that is disposed at atmospheric pressure (since it is open to atmospheric pressure 102 at one end) is defined by the vent 136 which is in direct communication with the channel 144 which is in direct communication with a portion 226 of the inner end 224 that is spaced from the center post 126 which is in direct communication with the vent passage 252 which is in direct communication with the opening 239.

The diaphragm 122 is movable between a vacuum orientation (see FIG. 7 which illustrates a cross-section view of the pump assembly of FIG. 2 disposed in a vacuum orientation) and a vent orientation (see FIG. 6 which illustrates a cross-section view of the pump assembly of FIG. 2 disposed in a vent orientation) in response to cyclic reciprocating movement of the piston assembly 120 by completing, on each cycle, a one hundred eighty degree bend and accumulating (by rolling the diaphragm 122) in the space defined by the first component of the inner surface of the piston housing 130, such that the vacuum orientation is defined when an outer opening 236 of the vent 136 is sealed (i.e., covered by or contiguous with the diaphragm so as to isolate the pressure chamber 146 on one side of the diaphragm from the permanently unobstructed continuous passageway 300 that extends across the diaphragm 122) by the rolled diaphragm 122 (see FIG. 7), and the vent orientation is defined when the outer opening 236 of the vent 136 is uncovered by the substantially unrolled diaphragm 122 so that the pressure chamber 146 is in direct communication with atmospheric pressure 102 via the permanently unobstructed continuous passageway 300 across the diaphragm 122. It will be recognized by one of skill in the art that when the pressure chamber 146 is at atmospheric pressure 102, the remainder of the breast pump system will also be disposed at atmospheric pressure (i.e., tubing, collection units 56, breast flanges 58, etc.), which creates a pleasing sensation to the user, which is akin to a suckling infant.

Figure 8:
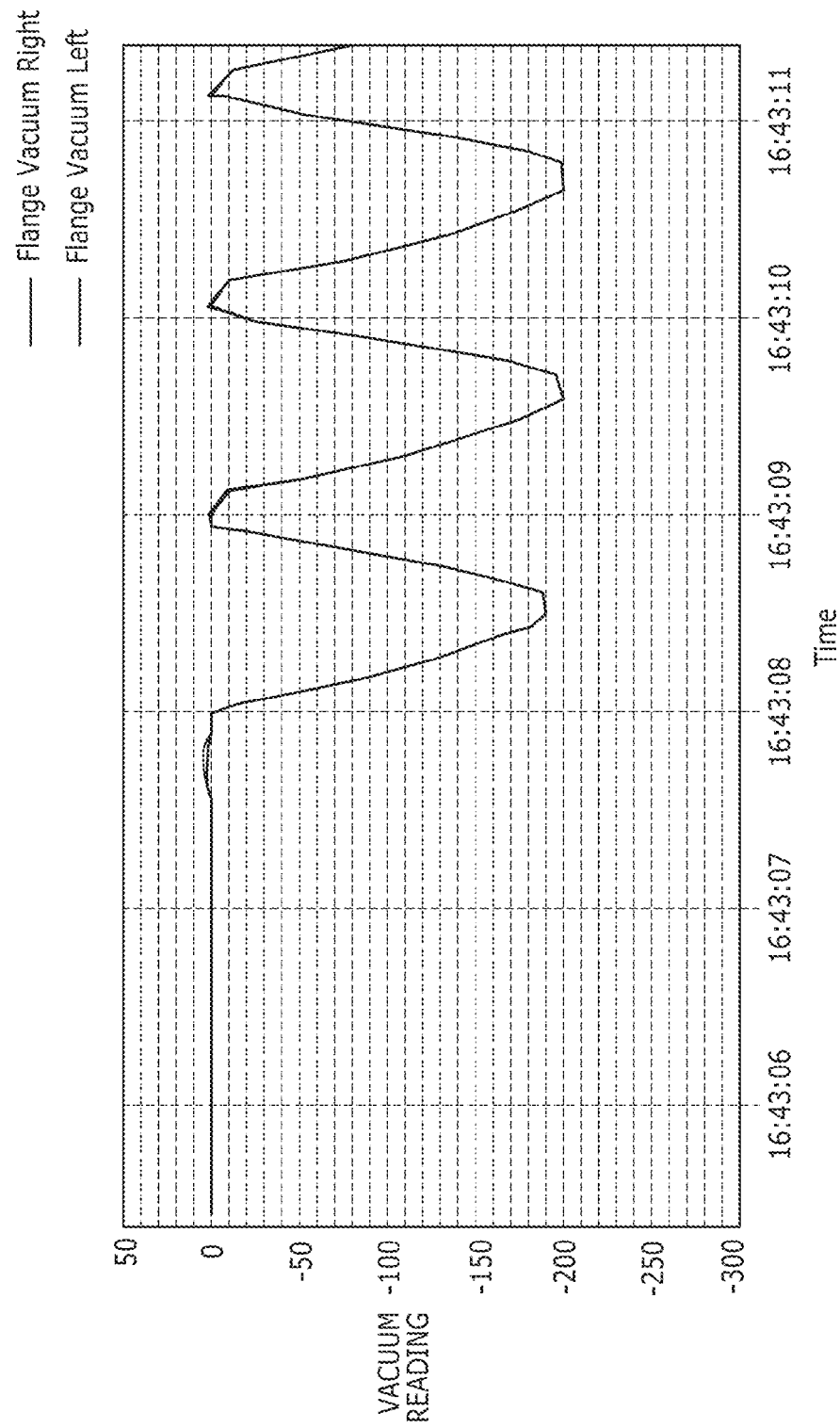
FIG. 8 is a graph of pressure versus time, illustrating a breast pump system vacuum recovery profile for one embodiment of the pump assembly of the present disclosure.

FIG. 8 is a graph of pressure versus time, illustrating a breast pump system vacuum recovery profile for one embodiment of the pump assembly 100 of the present disclosure. The two vacuum profile traces (i.e., for flange 58 vacuum left and flange 58 vacuum right) are nearly indistinguishable. One of skill in the art will recognize that this system is operating equivalently on both sides. Additionally, the maximum intended or desired vacuum (i.e., −200 mm Hg) for this test example only is reached immediately (i.e., in less than two complete cycles and less than 2 seconds). Furthermore, the maximum intended or desired vacuum is maintained at the constant level and the entire system is reset to atmospheric pressure on every cycle.

Figure 9:
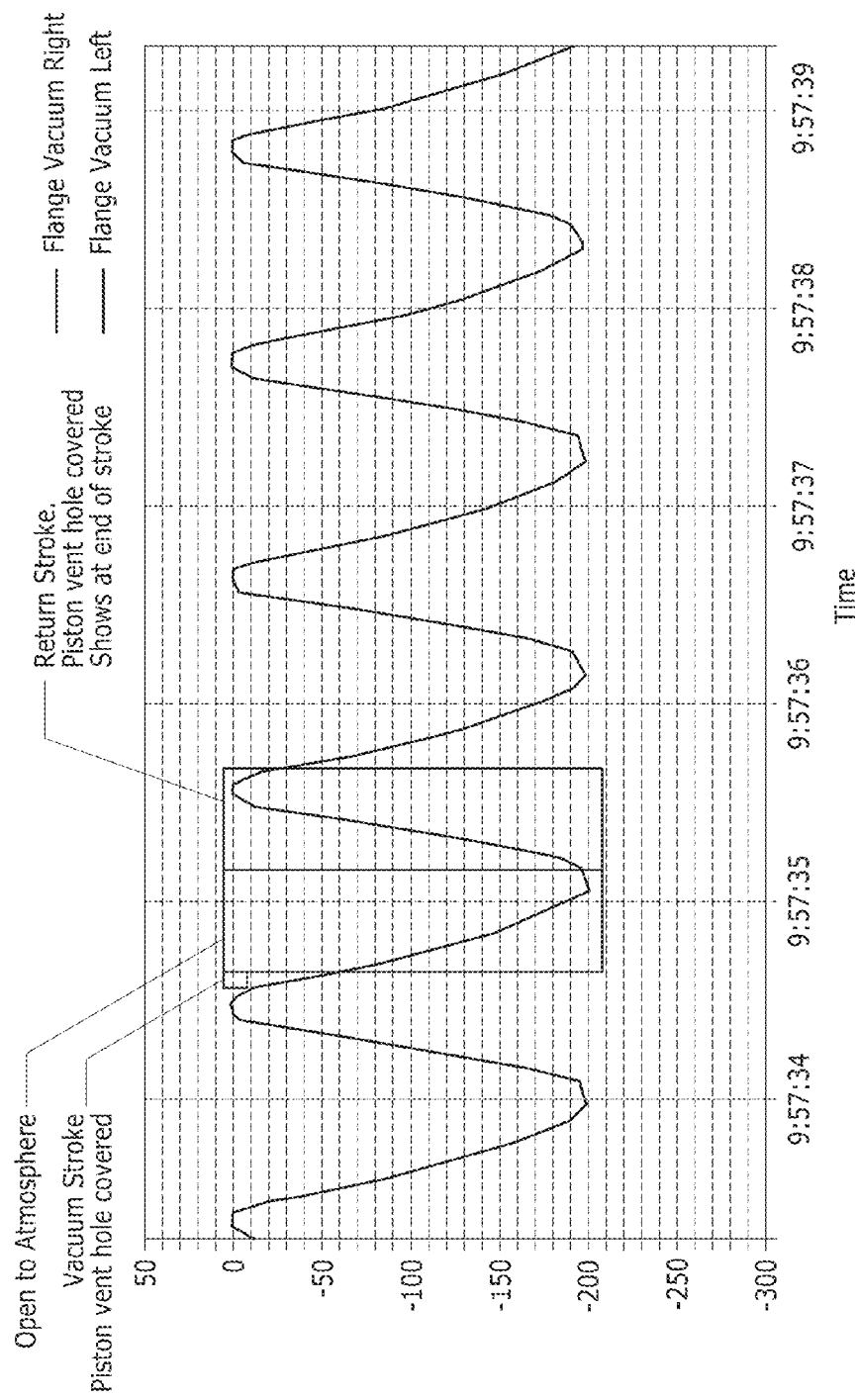
FIG. 9 is a graph of a pressure versus time, illustrating a breast pump system vacuum recovery profile for one embodiment of the pump assembly of the present disclosure with an annotated piston assembly cycle.

FIG. 9 is a graph of a pressure versus time, illustrating a breast pump system vacuum recovery profile for one embodiment of the pump assembly 100 of the present disclosure with an annotated piston assembly cycle. The first phase of the piston assembly 120 cycle is where the breast pump system is open to atmospheric pressure 102 across the diaphragm. In this disclosure, it is referred to as the vent orientation (see FIG. 6) where the vent orientation is defined when the outer opening 336 of the vent 136 is uncovered by the substantially unrolled diaphragm 122 so that the pressure chamber 146 is in direct communication with atmospheric pressure 102 via the permanently unobstructed continuous passageway 300 across the diaphragm 122. In one preferred embodiment, the diaphragm may be disposed in the vent orientation (FIG. 6) between approximately 0.1 seconds and 1.2 seconds of each cycle of the piston assembly, depending on the speed setting or the extent of the longitudinal displacement of the piston assembly. In yet another aspect, the diaphragm may be disposed in the vent orientation (FIG. 6) between approximately 15% to 60% of each cycle of the piston assembly, depending on the speed setting or the extent of the longitudinal displacement of the piston assembly. In a preferred embodiment, the diaphragm is disposed in the vent orientation (FIG. 6) between 0.2 seconds and 1.0 second, or between approximately 20% and 50% of each cycle of the piston assembly, depending on the speed setting or the extent of the longitudinal displacement of the piston assembly.

The second phase of the piston assembly 120 cycle is where the breast pump system builds a vacuum pressure in the pressure chamber 146 during a vacuum stroke. After the outer opening 236 of the vent 136 is sealed or covered by the overlapping diaphragm 122 when rolled, the pressure chamber 146 is no longer open to atmospheric pressure 102 and subsequent retraction of the piston assembly 120 from the end wall 235 creates vacuum pressure in the breast pump system since it is closed at the other end (i.e., breast flanges 58 against the breasts of the user) and the volume is increased. The distance that the piston assembly 120 is moved away from the end wall 235 correlates to the desired amount of vacuum that is desired to be generated in the system by the user. This desired amount is adjustable to the needs of the user.

The third phase of the piston assembly 120 cycle is where the breast pump system reduces the vacuum in the pressure chamber 146 during a return stroke. The piston assembly 120 is moved toward the end wall 235 to reduce the volume of the closed breast pump system and thereby increase the pressure or decrease the vacuum pressure present in the breast pump system to the same level as where the vacuum stroke started.

Then, the first phase starts again when the diaphragm is return to the vent orientation and the breast pump system is open to atmospheric pressure.

Figure 10A:
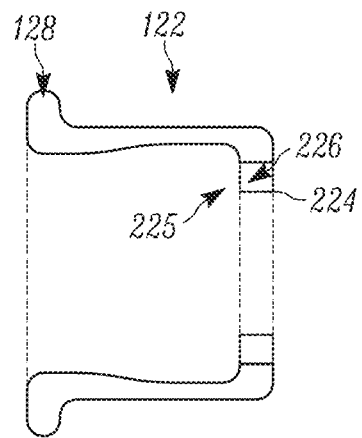
FIGS. 10A and 10B illustrate respective cross-section and bottom views of another embodiment of a diaphragm for a piston assembly of the present disclosure.
Figure 10B:
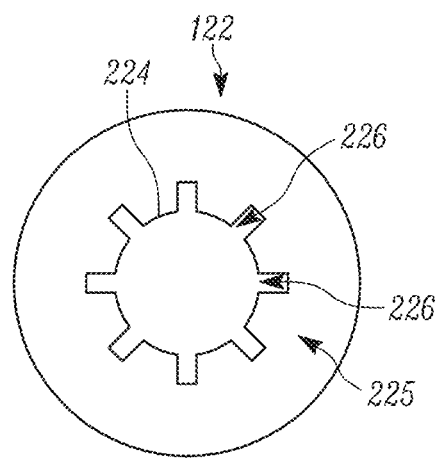

FIGS. 10A and 10B illustrate respective cross-section and bottom views of another embodiment of a diaphragm 122 for a piston assembly of the present disclosure. In this embodiment, the inner end 224 and the inner margin 225 of the diaphragm 122 have been configured such that the inner end 224 engages the center post 126 of the vent piston 134 and the portion 226 is configured as openings formed in the inner margin 225, so as to maintain the permanently unobstructed continuous passageway 300 across the diaphragm 122 for the advantages described herein. Otherwise, the remainder of the structure and functionality of the pump assembly 100 remains as described herein, when used in connection with this embodiment of the diaphragm 122. In particular, the inner edge 224 and portion 226 can be described as having a crenelated configuration and one of skill in the art will recognize that other similar configurations that provide the same functionality are within the scope of the present disclosure.

Figure 11A:
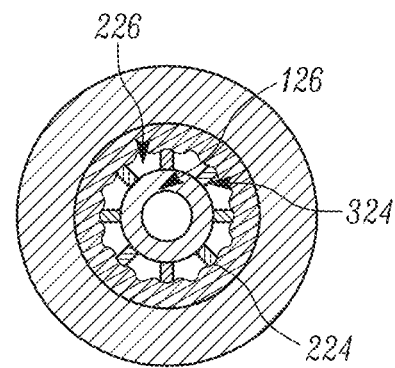
FIGS. 11A through 11I illustrate cross-section views of other embodiments of the piston assembly of the present disclosure.
Figure 11B:
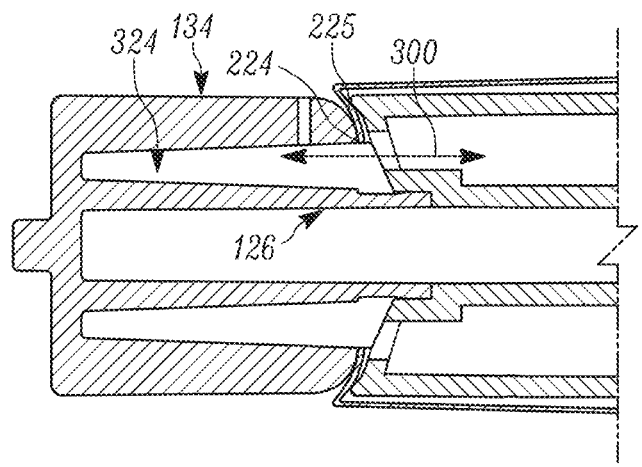

FIGS. 11A through 11I illustrate cross-section views of other embodiments of the piston assembly 120 of the present disclosure. FIGS. 11A and 11B illustrate respective bottom and cross-section views of another configuration of the piston assembly 120 where the center post 126 of the vent piston 134 includes a plurality of ribs 324 that extend radially therefrom into the channel 144 such that the inner end 224 of the diaphragm 122 circumferentially engage the ribs 324 and the portions 226 are disposed across the gap defined by adjacent ribs 324, so as to maintain the permanently unobstructed continuous passageway 300 across the diaphragm 122 for the advantages described herein. Otherwise, the remainder of the structure and functionality of the pump assembly 100 remains as described herein, when used in connection with this embodiment of the piston assembly 120.

Figure 11C:
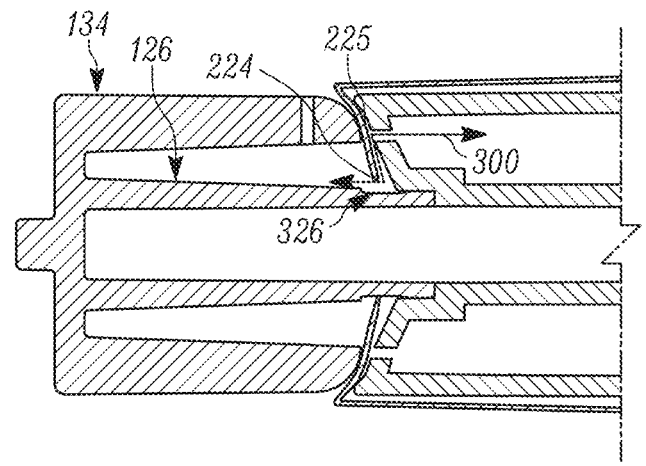

FIG. 11C illustrates a cross-section view of another embodiment of the piston assembly 120 of the present disclosure, where the center post 126 of the vent piston 134 has a recess 326 formed over a section adjacent the inner end 224, such that the inner end 224 of the diaphragm circumferentially engages the center post 126 other than the portion 226 adjacent the recess 326, so as to maintain the permanently unobstructed continuous passageway 300 across the diaphragm 122 for the advantages described herein. Otherwise, the remainder of the structure and functionality of the pump assembly 100 remains as described herein, when used in connection with this embodiment of the piston assembly 120.

Figure 11D:
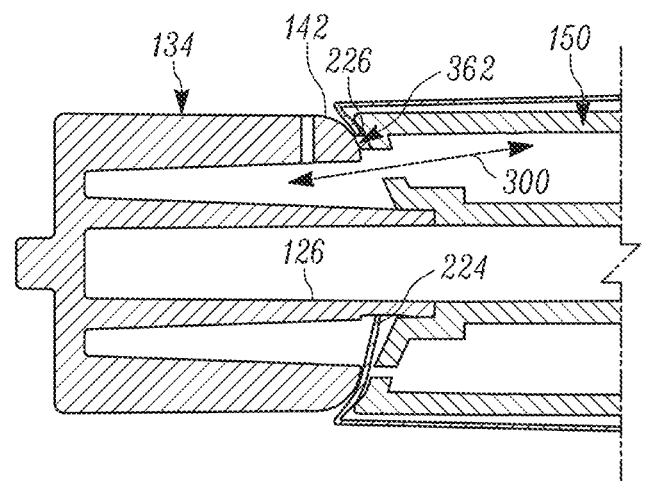

FIG. 11D illustrates a cross-section view of another embodiment of the piston assembly 120 of the present disclosure, where the vent piston 134 include a projection 362 extending from the side wall 142 into contact with the drive piston 150 such that the inner end engages the center post 126 other than the portion 226 that engages the projection 362, so as to maintain the permanently unobstructed continuous passageway 300 across the diaphragm 122 for the advantages described herein. Otherwise, the remainder of the structure and functionality of the pump assembly 100 remains as described herein, when used in connection with this embodiment of the piston assembly 120.

Figure 11E:
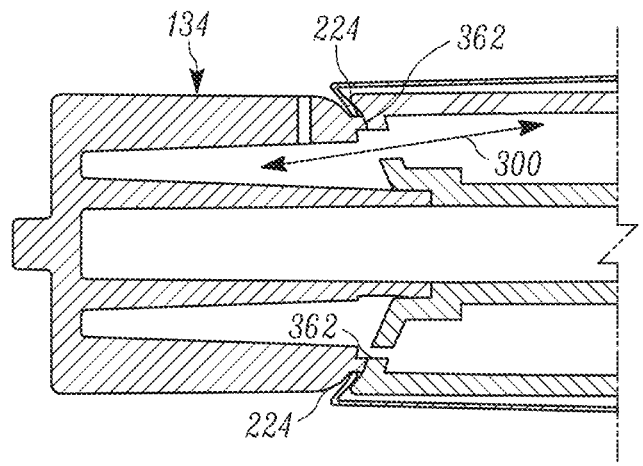

FIG. 11E illustrates a cross-section view of another embodiment of the piston assembly 120 of the present disclosure, where the vent piston 134 include a projection 362 extending from the side wall 142 about the circumference of the vent piston 134 into contact with the drive piston 150 such that the inner edge 224 engages the projection 362, so as to maintain the permanently unobstructed continuous passageway 300 across the diaphragm 122 for the advantages described herein. Otherwise, the remainder of the structure and functionality of the pump assembly 100 remains as described herein, when used in connection with this embodiment of the piston assembly 120.

Figure 11F:
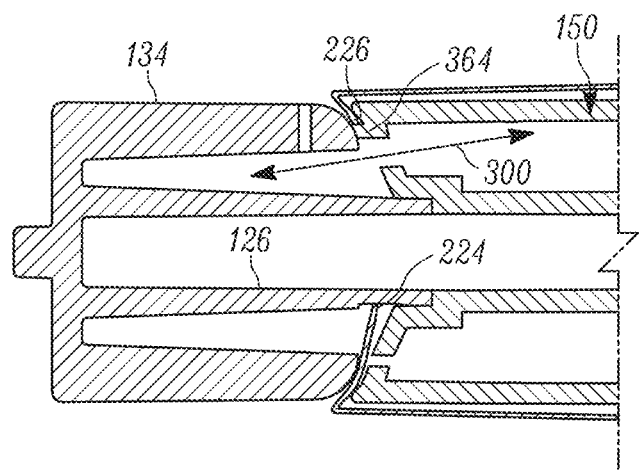

FIG. 11F illustrates a cross-section view of another embodiment of the piston assembly 120 of the present disclosure, where the drive piston 150 include an extension 364 that projects from the top wall 251 into contact with the vent piston 134 such that the inner end 224 engages the center post 126 other than the portion 226 that engages the extension 364, so as to maintain the permanently unobstructed continuous passageway 300 across the diaphragm 122 for the advantages described herein. Otherwise, the remainder of the structure and functionality of the pump assembly 100 remains as described herein, when used in connection with this embodiment of the piston assembly 120.

Figure 11G:
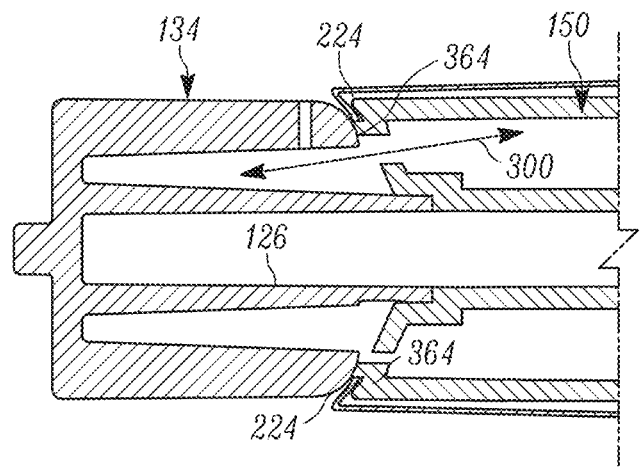

FIG. 11G illustrates a cross-section view of another embodiment of the piston assembly 120 of the present disclosure, where the drive piston 150 include an extension 364 that projects from the top wall 251 about the circumference of the drive piston 150 into contact with the vent piston 134 such that the inner end 224 circumferentially engages the extension 364, so as to maintain the permanently unobstructed continuous passageway 300 across the diaphragm 122 for the advantages described herein. Otherwise, the remainder of the structure and functionality of the pump assembly 100 remains as described herein, when used in connection with this embodiment of the piston assembly 120.

Figure 11H:
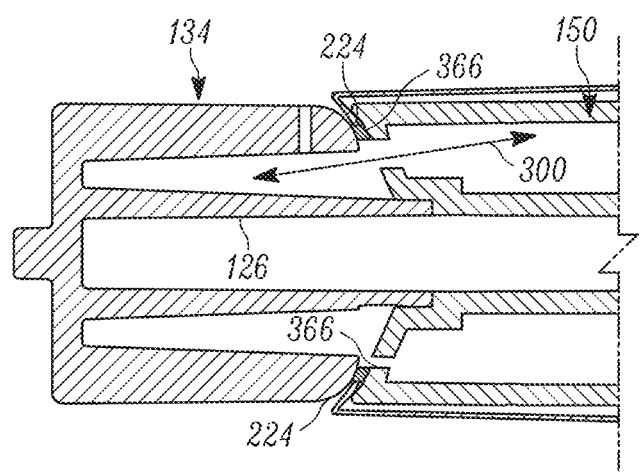

FIG. 11H illustrates a cross-section view of another embodiment of the piston assembly 120 of the present disclosure, where an insert 366 is disposed between and contiguous with the vent piston 134 and the drive piston 150 about the circumference of the vent piston 134 and the drive piston 150 such that the inner end engages the engages the insert 366, so as to maintain the permanently unobstructed continuous passageway 300 across the diaphragm 122 for the advantages described herein. Otherwise, the remainder of the structure and functionality of the pump assembly 100 remains as described herein, when used in connection with this embodiment of the piston assembly 120.

Figure 11I:
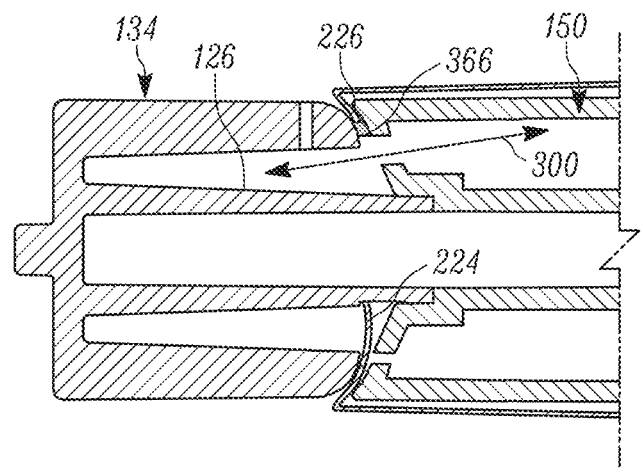

FIG. 11I illustrates a cross-section view of another embodiment of the piston assembly 120 of the present disclosure, where an insert 366 is disposed between and contiguous with the vent piston 134 and the drive piston 150 about a section of the circumference of the vent piston 134 and the drive piston 150 such that the inner end engages the center post 126 other than the portion 226 that engages the insert 366, so as to maintain the permanently unobstructed continuous passageway 300 across the diaphragm 122 for the advantages described herein. Otherwise, the remainder of the structure and functionality of the pump assembly 100 remains as described herein, when used in connection with this embodiment of the piston assembly 120.

Figure 12:
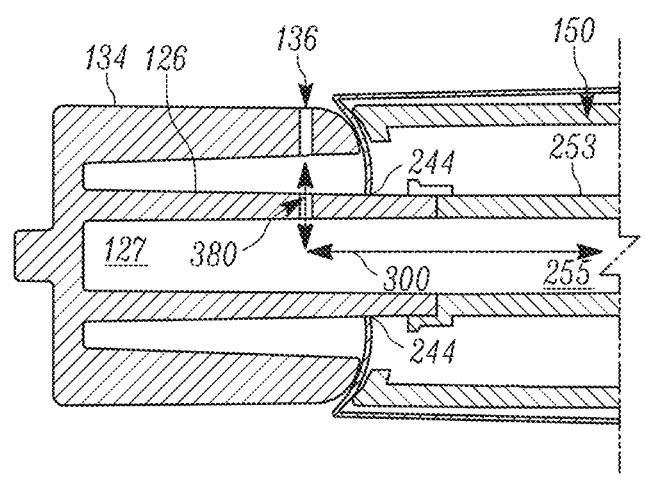
FIG. 12 illustrates a cross-section view of another embodiment of piston assembly of the present disclosure including a drive screw having a bore.

FIG. 12 illustrates a cross-section view of another embodiment of piston assembly 120 of the present disclosure including the vent piston 134 having a hollow center post 126 where a second vent 380 is defined to extend through a wall of the center post 126 into the hollow 127. The drive piston 150 has a hollow center post 253 with a vent passage 254 defined therethrough. Preferably, the hollow center posts 126, 254 of the vent piston 134 and the drive piston 150 are longitudinally aligned in registration and sealingly connected, such that a permanently unobstructed continuous passageway 300 across the diaphragm 122 that is disposed at atmospheric pressure defined by the vent 136 in direct communication with the channel 144 in direct communication with the second vent 380 in direct communication with the hollow 127 of the center post 126 of the vent piston 134 direct communication with the hollow 255 of the center post 253 of the drive piston 150 and the opening 239. Otherwise, the remainder of the structure and functionality of the pump assembly 100 remains as described herein, when used in connection with this embodiment of the piston assembly 120.

Figure 13A:
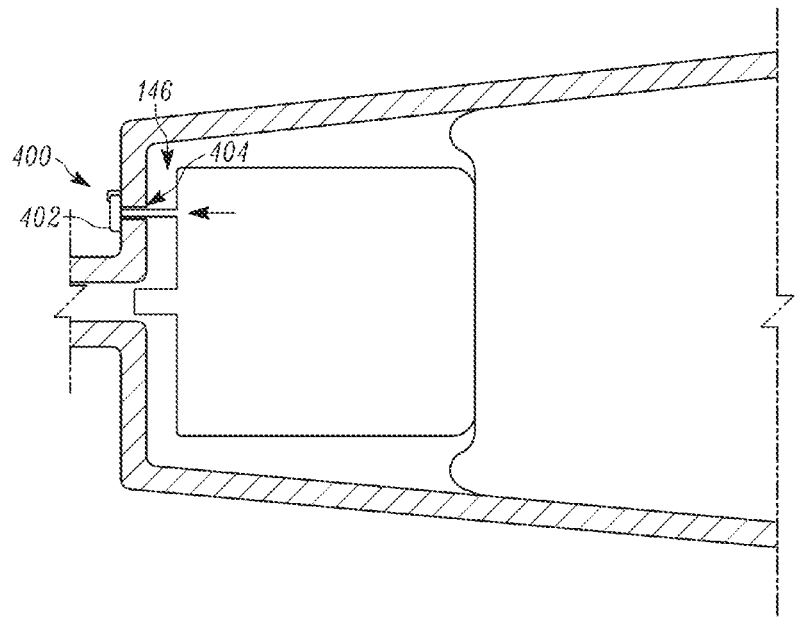
FIGS. 13A and 13B illustrate cross-section views of embodiments of a dynamic vent for the pump assembly of the present disclosure.
Figure 13B:
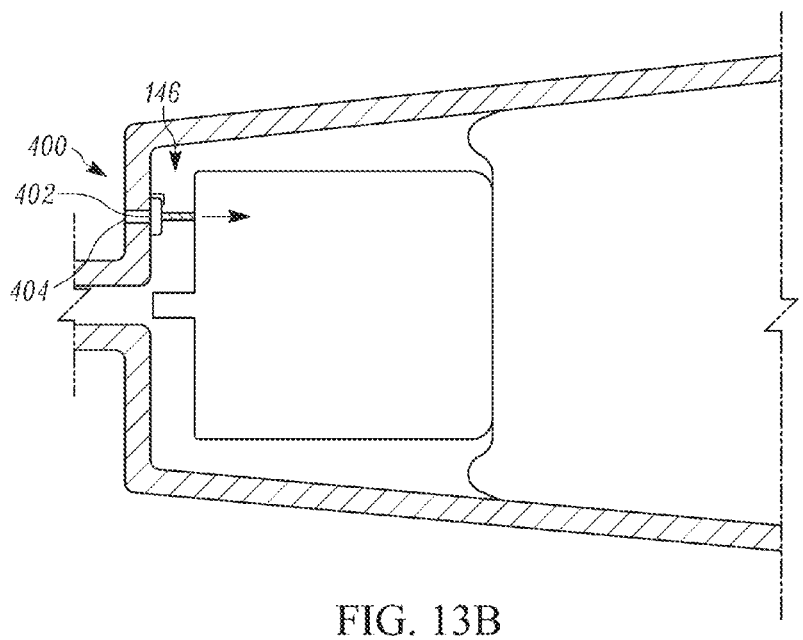

FIGS. 13A and 13B illustrate cross-section views of embodiments of a dynamic vent 400 for the pump assembly 100 of the present disclosure. The vent piston 134 is configured to actuate a closure 402 between a vent orientation and a vacuum orientation, wherein the vent orientation is defined when the vent piston 134 actuates the closure 402 to open the vent passage 404 so that the pressure chamber 146 is in direct communication with atmospheric pressure 102 and the vacuum orientation is defined when the vent piston 134 is disengaged from the closure 402. One of skill in the art will recognize that the closure in this embodiment is configured as a flap that covers and uncovers an opening based on movement of the vent piston 134 and a projection or tether associated with the vent piston 134 and the closure 402, and that any other suitable structure to facilitate the intended functionality is within the teachings of the present disclosure.

The above detailed description and the examples described therein have been presented for the purposes of illustration and description only and not by limitation. It is therefore contemplated that the present disclosure cover any and all modifications, variations or equivalents that fall within the spirit and scope of the basic underlying principles disclosed above and claimed herein

The invention claimed is:

1. A breast pump assembly comprising:
 a housing assembly including a piston housing and a drive housing having an opening in direct communication with atmospheric pressure;
 a piston assembly including a vent piston and a drive piston, the vent piston having a top wall and a channel defined by the top wall, a side wall and a center post where a vent is defined to extend through the side wall in communication with the channel, the drive piston having a top wall with a vent passage defined therethrough;
 a rolling diaphragm including an outer end, an outer margin disposed adjacent the outer end, where both of the outer end and outer margin are sealingly captured between the piston housing and the drive housing, an inner end, and an inner margin disposed adjacent the inner end, where the inner margin is sealingly captured between the vent piston and the drive piston to cooperatively define a pressure chamber between the diaphragm, piston housing and vent piston; and a permanently unobstructed continuous passageway across the diaphragm that is disposed at atmospheric pressure defined by the vent in direct communication with the channel, the channel in direct communication with a portion of the inner end that is spaced from the center post, and the vent passage in direct communication with the inner end portion and the opening, wherein the diaphragm is movable between a vacuum orientation and a vent orientation in response to cyclic movement of the piston assembly, such that the vacuum orientation is defined when an outer opening of the vent is sealed by the diaphragm, and the vent orientation is defined when the outer opening of the vent is uncovered by the diaphragm so that the pressure chamber is in direct communication with atmospheric pressure via the permanently unobstructed continuous passageway across the diaphragm, and wherein the diaphragm is disposed in the vent orientation between 15% and 60% of each cycle of the piston assembly.

2. The breast pump assembly of claim 1, wherein the portion is the entirety of the inner end.

3. The breast pump assembly of claim 1, wherein the portion is defined by the inner end having a crenelated contour.

4. The breast pump assembly of claim 2, wherein a plurality of ribs extend from the center post to engage the inner end.

5. The breast pump assembly of claim 1, wherein the center post has a recess formed over a section adjacent the inner end.

6. The breast pump assembly of claim 1, wherein the vent piston includes a projection extending from the side wall into contact with the drive piston such that the portion engages the projection.

7. The breast pump assembly of claim 2, wherein the vent piston includes a projection extending from the side wall into contact with the drive piston such that the inner edge engages the projection.

8. The breast pump assembly of claim 1, wherein the drive piston includes an extension that projects from the top wall into contact with the vent piston such that the portion engages the extension.

9. The breast pump assembly of claim 2, wherein the drive piston includes an extension that projects from the top wall into contact with the vent piston such that the inner edge engages the extension.

10. The breast pump assembly of claim 1, wherein an insert is disposed between the drive piston and the vent piston such that the portion engages the insert.

11. The breast pump assembly of claim 2, wherein the an insert is disposed between the drive piston and the vent piston such that the inner edge engages the insert.

* * * * *